US011389075B2

(12) United States Patent
Nerone

(10) Patent No.: US 11,389,075 B2
(45) Date of Patent: Jul. 19, 2022

(54) VETERINARY PULSE PROBE

(71) Applicant: Louis Robert Nerone, Brecksville, OH (US)

(72) Inventor: Louis Robert Nerone, Brecksville, OH (US)

( * ) Notice: Subject to any disclaimer, the term of this patent is extended or adjusted under 35 U.S.C. 154(b) by 0 days.

(21) Appl. No.: 17/446,783

(22) Filed: Sep. 2, 2021

(65) Prior Publication Data

US 2022/0151505 A1    May 19, 2022

Related U.S. Application Data

(60) Provisional application No. 63/198,862, filed on Nov. 18, 2020.

(51) Int. Cl.
| | |
|---|---|
| *A61B 5/02* | (2006.01) |
| *A61B 5/024* | (2006.01) |
| *A61B 5/021* | (2006.01) |
| *A61B 5/00* | (2006.01) |
| *A61B 5/026* | (2006.01) |

(52) U.S. Cl.
CPC .......... *A61B 5/02433* (2013.01); *A61B 5/021* (2013.01); *A61B 5/0261* (2013.01); *A61B 5/7405* (2013.01); *A61B 5/7455* (2013.01); *A61B 2503/40* (2013.01)

(58) Field of Classification Search
CPC ... A61B 5/02433; A61B 5/021; A61B 5/0261; A61B 5/7405; A61B 5/7455; A61B 2503/40

See application file for complete search history.

(56) References Cited

U.S. PATENT DOCUMENTS

| | | | |
|---|---|---|---|
| 3,769,974 A | 11/1973 | Smart et al. | |
| 3,835,837 A * | 9/1974 | Peek | A61B 5/024 600/479 |
| 5,800,349 A * | 9/1998 | Isaacson | A61B 5/14552 600/323 |
| 6,436,038 B1 | 8/2002 | Engstrom | |
| 7,524,290 B2 | 4/2009 | Ide | |
| 7,762,953 B2 | 7/2010 | Derchak et al. | |
| 8,005,624 B1 | 8/2011 | Starr | |
| 10,292,593 B2 | 5/2019 | Razansky et al. | |
| 10,492,473 B2 | 12/2019 | Menkes et al. | |
| 10,779,510 B1 | 9/2020 | Moss et al. | |
| 2002/0010390 A1 | 1/2002 | Guice et al. | |

(Continued)

*Primary Examiner* — Andrey Shostak
(74) *Attorney, Agent, or Firm* — Dunlap Bennett & Ludwig, PLLC; Anna L. Kinney

(57) ABSTRACT

A noninvasive method of sensing an arterial pulse on a paw pad includes providing an instrument having a probe; placing the probe housing a tactile transducer and a reflective optical coupler comprising an infrared emitter and an infrared detector on a subject's metatarsal or metacarpal pad; emitting infrared light from the emitter; detecting infrared light with the detector; maintaining a linear direct current bias of the detector; converting a signal emitted by the infrared detector into a digital pulse that drives the tactile transducer to emit tactile pulses; and counting the tactile pulses over a predetermined time. An arterial pulse detection system includes a probe. The probe contains an optical sensor and a tactile transducer to which instrumentation is electrically connected. The optical sensor includes an infrared emitter and an infrared detector.

11 Claims, 6 Drawing Sheets

(56) References Cited

U.S. PATENT DOCUMENTS

| | | |
|---|---|---|
| 2005/0096557 A1 | 5/2005 | Vosburgh et al. |
| 2008/0258923 A1 | 10/2008 | Sato |
| 2010/0145170 A1 | 6/2010 | Ayers et al. |
| 2011/0313264 A1 | 12/2011 | Hete |
| 2012/0143071 A1 | 6/2012 | Hete et al. |
| 2013/0201021 A1* | 8/2013 | Limonadi .......... A63B 21/0407 340/573.7 |
| 2016/0331329 A1* | 11/2016 | Hiroshima ............ A61B 5/7225 |
| 2017/0039822 A1* | 2/2017 | Schlesinger ............. H03G 3/32 |
| 2017/0055880 A1* | 3/2017 | Agrawal ............... A61B 5/6807 |
| 2019/0099009 A1* | 4/2019 | Connor ................ A47C 21/048 |
| 2019/0365302 A1* | 12/2019 | Burnett ................ A61B 5/6814 |
| 2020/0107734 A1 | 4/2020 | Young et al. |
| 2021/0161441 A1* | 6/2021 | Waltman ................ A61B 5/083 |

\* cited by examiner

VETERINARY PULSE PROBE

CROSS-REFERENCE TO RELATED APPLICATION

This application claims the benefit of priority of U.S. provisional application No. 63/198,862, filed Nov. 18, 2020, the contents of which are herein incorporated by reference.

BACKGROUND OF THE INVENTION

The present invention relates to a device for detecting pulse and thereby estimating the heart rate in beats per minute or facilitate measuring the blood pressure and, more particularly, to a veterinary pulse probe.

Human arterial blood pressure can be estimated by applying external pressure to the arm, just above the elbow, while listening for vibrations in the brachial artery. Without pressure, there are no audible vibrations. When pressure is applied at an increasing rate, blood flow through the artery is partially obstructed, causing it to vibrate. This vibration can be heard through a stethoscope. At this pressure, the pulse can be measured by counting the vibrations. Increasing the pressure further will completely occlude the artery whereby the vibrations will cease. The pressure that completely occludes the artery is the systolic pressure. Although this non-invasive, auscultatory method has been used since the 19th century, it does not work on small animals. The vibrations are too faint to be heard with a stethoscope.

Estimating systolic blood pressure is essential to Veterinary care. Elevated blood pressure caused by Chronic Kidney Disease, Hyperthyroidism, Diabetes, or Idiopathic conditions can be life threatening. The Veterinarian may prescribe medication based on the systolic pressure. Too much medication may inhibit the function of the susceptible organs like the kidneys. Little or no medication when it is needed can accelerate the progression of the disease or cause other organs to fail. Accurate measurements, without undue stress, are therefore important.

The unfamiliar clinical environment often elevates the pet's blood pressure. Therefore, a blood pressure measurement under familiar surroundings is very important. The pressure is measured by detecting the pulse in a limb while applying external pressure via a cuff. Unlike human measurements, the pulse of small animals cannot be detected in the limbs by auscultatory means whereby arterial vibrations are heard in a stethoscope.

Veterinarians use Doppler probes to measure the pulse and consequently determine the blood pressure by applying external pressure to a cuff. The Doppler instrument has an aural output only, from a built-in speaker or optionally through earphones. Doppler instruments are very expensive, beyond the means of most pet parents. In addition, to couple the high frequency acoustic wave to the vascular region of the skin, ultrasound gel is applied. Sometimes the fur must be shaved. These techniques add to clinical stress.

The Oscillometric method is much less costly and has been tried by pet parents at home. The Oscillometric method does not work well in small animals, under 25 pounds, like most cats. The instrument is unable to discern a pressure variation caused by the pulsating artery from minor motions in the limb. The animal must remain motionless to obtain an accurate measurement, an unlikely state as the measurement progresses. Oscillometric devices cannot measure the pulse without external pressure.

The human pulse can be measured by palpating the vibrating radial artery with two fingers. The faint vibrations in the radial or ulnar arteries in a small animal cannot be felt. Tactile sensing is analogous to palpating the artery. No tactile sensing device, with a probe to detect blood flow, is commercially available.

As can be seen, there is a need for an accurate, inexpensive method to measure systolic pressure in familiar home surroundings.

SUMMARY OF THE INVENTION

The present invention provides a system comprising a probe and instrumentation operative to detect a heartbeat when placed on the metatarsal or metacarpal pad of a subject, a convenient location that is open to pulse detection. The inventive system provides a tactile or aural means (with an earphone) of detecting the pulse which is otherwise undetectable in small animals by palpation. Tactile sensing provides a quiet, non-invasive, and accurate method of detecting the heartbeat. The present invention enables confident, at-home measurements of a cat or a dog pulse and/or heartbeat, so that a pet parent may measure the heart rate or detect the systolic blood pressure under a familiar home environment, free of stress. The instrument is very portable, about the size of a small pocket radio. It may be taken to the clinic to verify its accuracy. The present invention may also be used to detect human heart pulses and facilitate measuring human systolic blood pressure, especially in neonatal care.

The inventive system is much less sensitive to motion than oscillometric instruments if the transducer remains in contact with the metatarsal or metacarpal pad. Unlike Doppler means, ultrasound gel and shaving the fur at the detection area are not required. The pulse may be detected without external pressure, which provides a non-invasive method of measuring the heart rate. The cost is very low, well within the means of most pet parents.

In one aspect of the present invention, a noninvasive method of sensing an arterial pulse on a paw pad is provided comprising providing an instrument having a probe housing a reflective optical coupler comprising an infrared emitter and an infrared detector, and a tactile transducer; placing the probe on a metatarsal pad or a metacarpal pad of a subject; emitting infrared light from the infrared emitter; detecting infrared light with the infrared detector; maintaining a linear direct current bias of the infrared detector; and converting a signal emitted by the infrared detector into a digital pulse that drives the tactile transducer to emit tactile pulses.

In another aspect of the present invention, an arterial pulse detection system is provided, comprising a probe having a probe housing containing an optical sensor comprising an infrared emitter and an infrared detector; a tactile transducer operative to convert a signal received from the infrared detector to a vibratory pulse; and instrumentation electrically connected to the optical sensor and the tactile transducer.

These and other features, aspects and advantages of the present invention will become better understood with reference to the following drawings, description, and claims.

DETAILED DESCRIPTION OF THE INVENTION

Figure 1:
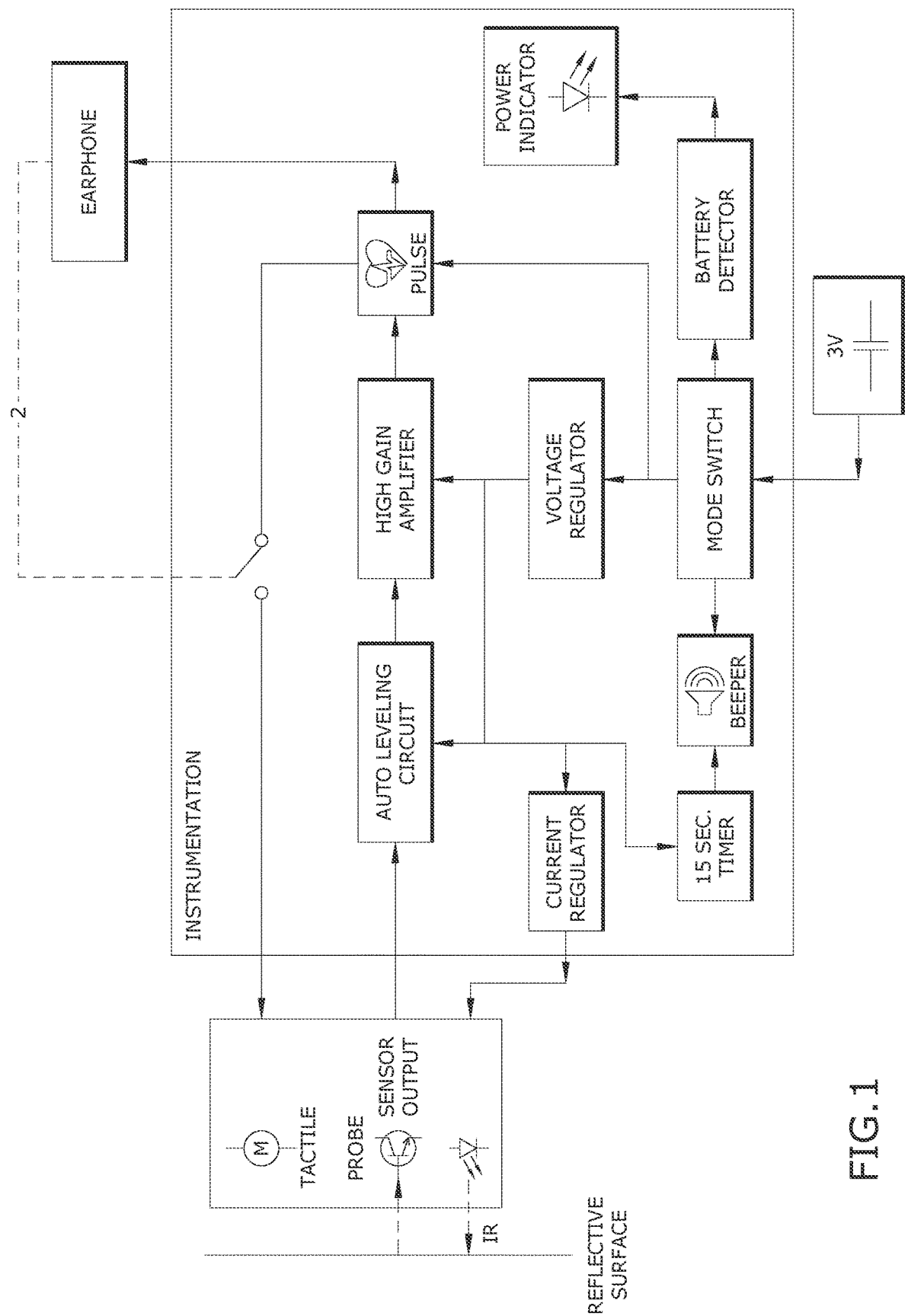
FIG. 1 is a block diagram illustrating a pulse detection system according to an embodiment of the present invention.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a probe comprising a blood flow sensor for detecting the arterial pulse and heartbeat via a metatarsal or metacarpal paw pad and a tactile transducer for tactile output contained within a probe housing. An earphone may alternatively be used with the probe for auditory output. The probe includes an optical (infrared) blood flow detector (heart rate and/or pulse) and a tactile transducer that producers a vibration corresponding to the pulse. The vibration may be felt by the measurer.

The system may operate as follows. An optical sensor is a reflective optical coupler comprising an infrared emitter, such as a light emitting diode (LED), and a laterally positioned phototransistor, i.e., an infrared detector. The optical sensor detects vascular flow below the epidermal layer in the subject's metacarpal or metatarsal pad using infrared light produced by the infrared emitter and reflected to the phototransistor. Pulsating blood flow, produced by a beating heart, causes perturbations of the light detected by the phototransistor. The light perturbations cause current to vary in the phototransistor, around the bias current. The high gain amplifier amplifies these variations, producing a digital pulse. The pulse generating circuit is coupled to the vibration motor M which produces tactile vibrations that coincide with the pulse.

Power may be applied by a switch to activate instrumentation. The measurer may touch the probe to the metatarsal or metacarpal pad. Pulsations produced by the vibration motor represent the heartbeat and may be felt in the probe within a few seconds.

The instrumentation may include an auto-leveling circuit. With cats and small dogs, the probe may lose contact with the pad and be exposed to ambient light until the probe contacts with the pad again. Without an auto-leveling circuit the phototransistor saturates causing a delay with the detection of the pulse. With this auto-leveling method, the phototransistor is always maintained in its linear mode, well out of saturation or cutoff, regardless of the ambient light or variations in the pigmentation of the pad.

The earphones produce a pulsation audible to the user. The instrumentation may produce a pulse corresponding to the heartbeat, rather than a sinusoidal excitation of the earphone. The transducer of the earphone "rings" in response to the edges of the pulse, similar to auscultatory means. This "ringing" near the transducer's resonant frequency is audible within the human spectrum as a clicking sound. A click may be heard at each transition of the heart, first the contraction and then the relaxation of the heart muscle. Therefore, two pulses may be heard, closely spaced temporally, followed by an elongated quiet period. The volume may be controlled (modulated) by a potentiometer, which may be part of a power switch.

The user may choose an earphone-only setting to detect the pulsations of the heart.

In some embodiments, when an earphone is inserted into an earphone jack on an instrumentation housing, a switch disconnects the tactile transducer and routes the signal from the transducer into the earphone.

The user may choose a tactile-only setting to detect the pulsations of the heart.

The instrument dimensions are not particularly limited. Preferably, the dimensions are small, making the instrument very portable. For example, the device may be about 3.5"× about 2.5"×about 1.2".

The instrumentation may comprise a battery detector that measures the battery voltage. The battery detector may include a logic gate. When power is applied through the power switch, if the voltage is between 2.6-3.0 volts of direct current (VDC), a power indicator lamp may be lit continuously. If the battery voltage falls below 2.6 VDC, the power indicator lamp may flash at about a 1 second rate. The flashing lamp informs the user to replace the batteries. For example, the inventive device may use about 2 double-A (AA) alkaline batteries.

To measure systolic pressure, the inventive probe may be used with a blood pressure cuff and a sphygmomanometer, that has a pressure gauge calibrated, for example, in mm of Hg. The blood pressure cuff may be wrapped around the femur region of the limb, for example, and inflated with the sphygmomanometer to apply pressure. The inventive probe may be used to detect the pulse either by tactile or aural means. The user may count the number of tactile pulses over a predetermined time to get beats per minute. The user may apply pressure until the pulses cease, indicating that the artery is occluded. The user may then slowly deflate the cuff with the sphygmomanometer just until the pulses return. This is the systolic pressure. The cuff may then be deflated completely.

Figure 2:
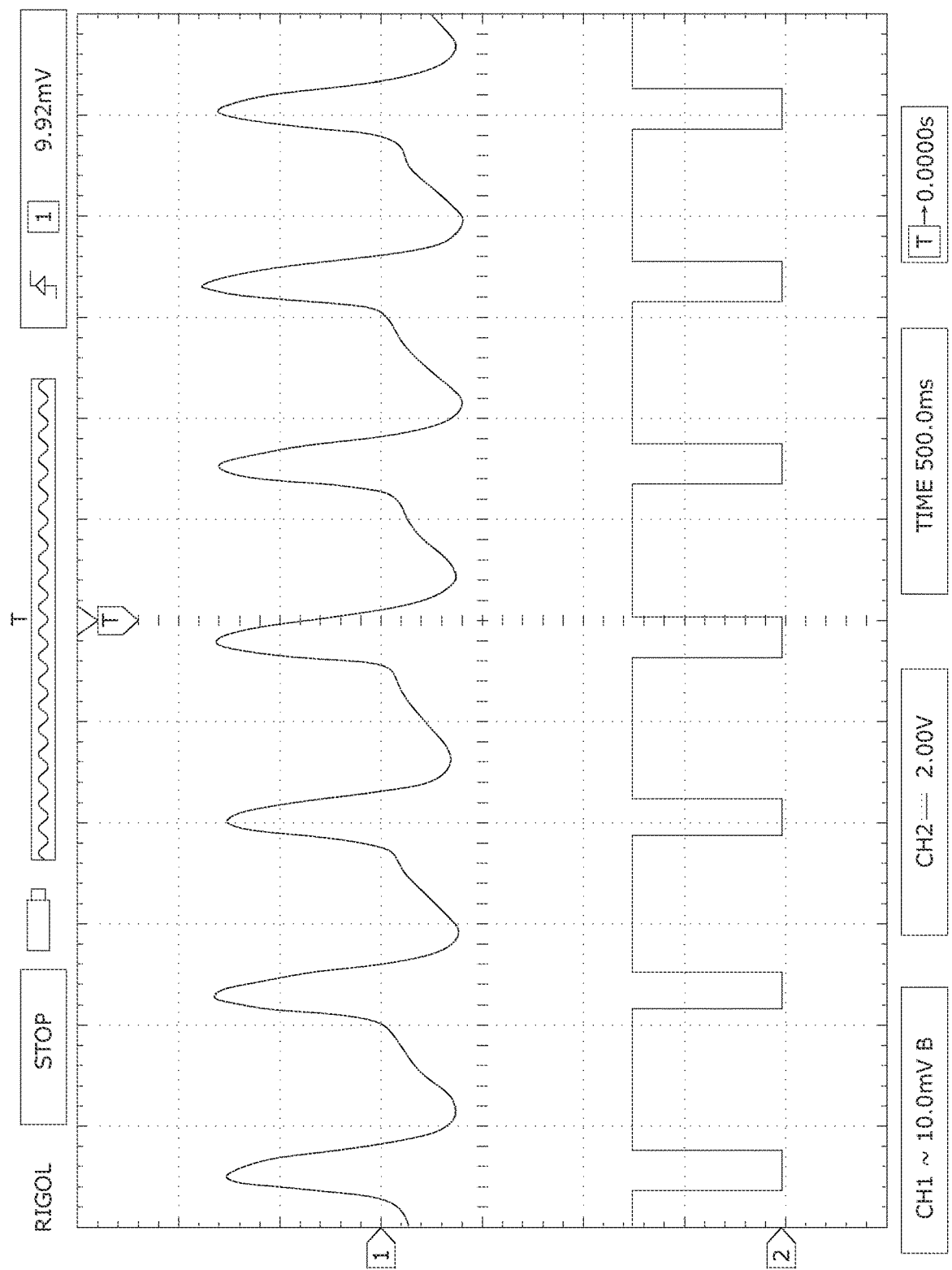
FIG. 2 is a schematic of sensor output illustrative of data obtained by the inventive system.
Figure 3:
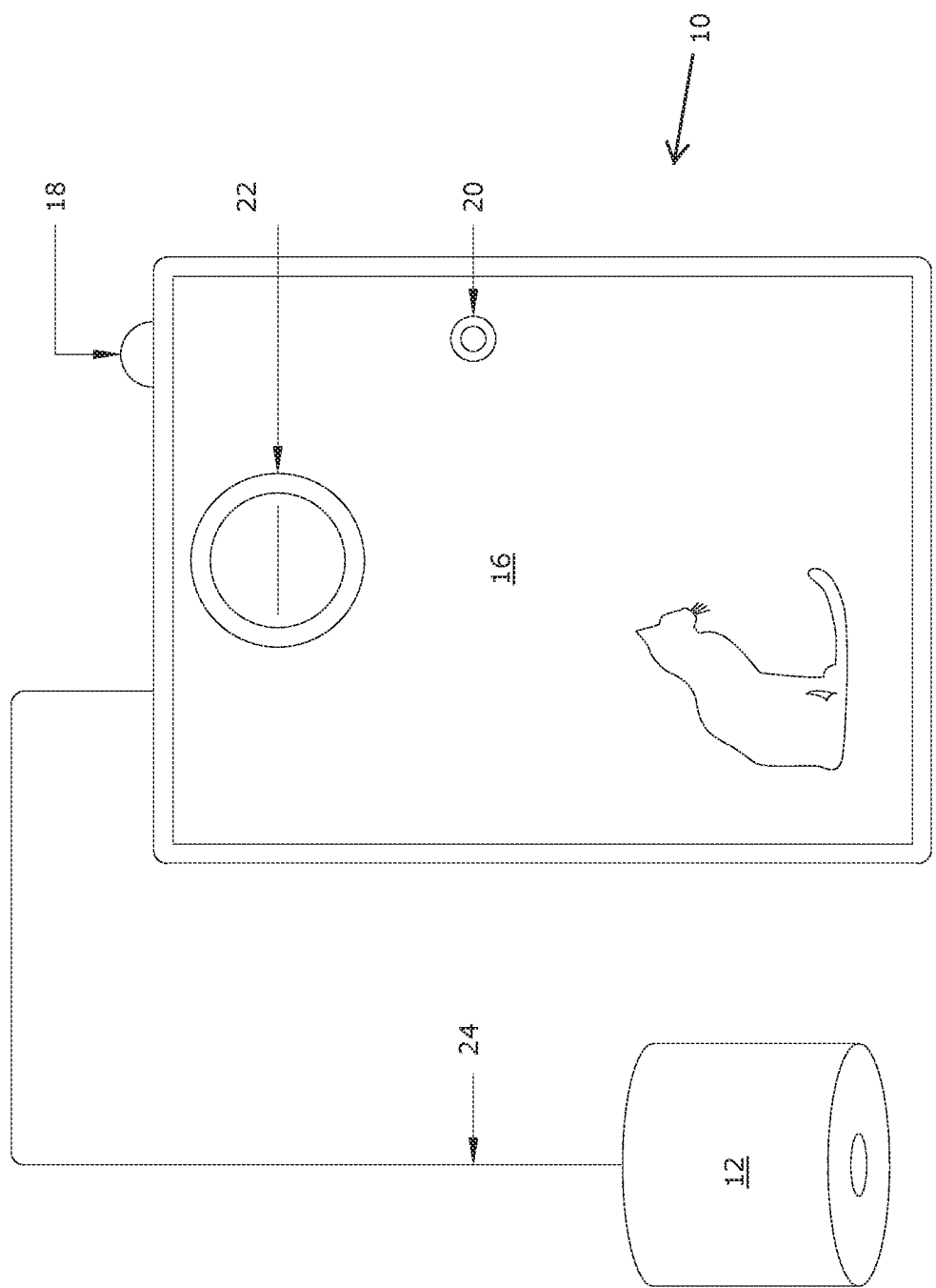
FIG. 3 is a front elevation view of a pulse detection instrument according to an embodiment of the present invention.
Figure 4:
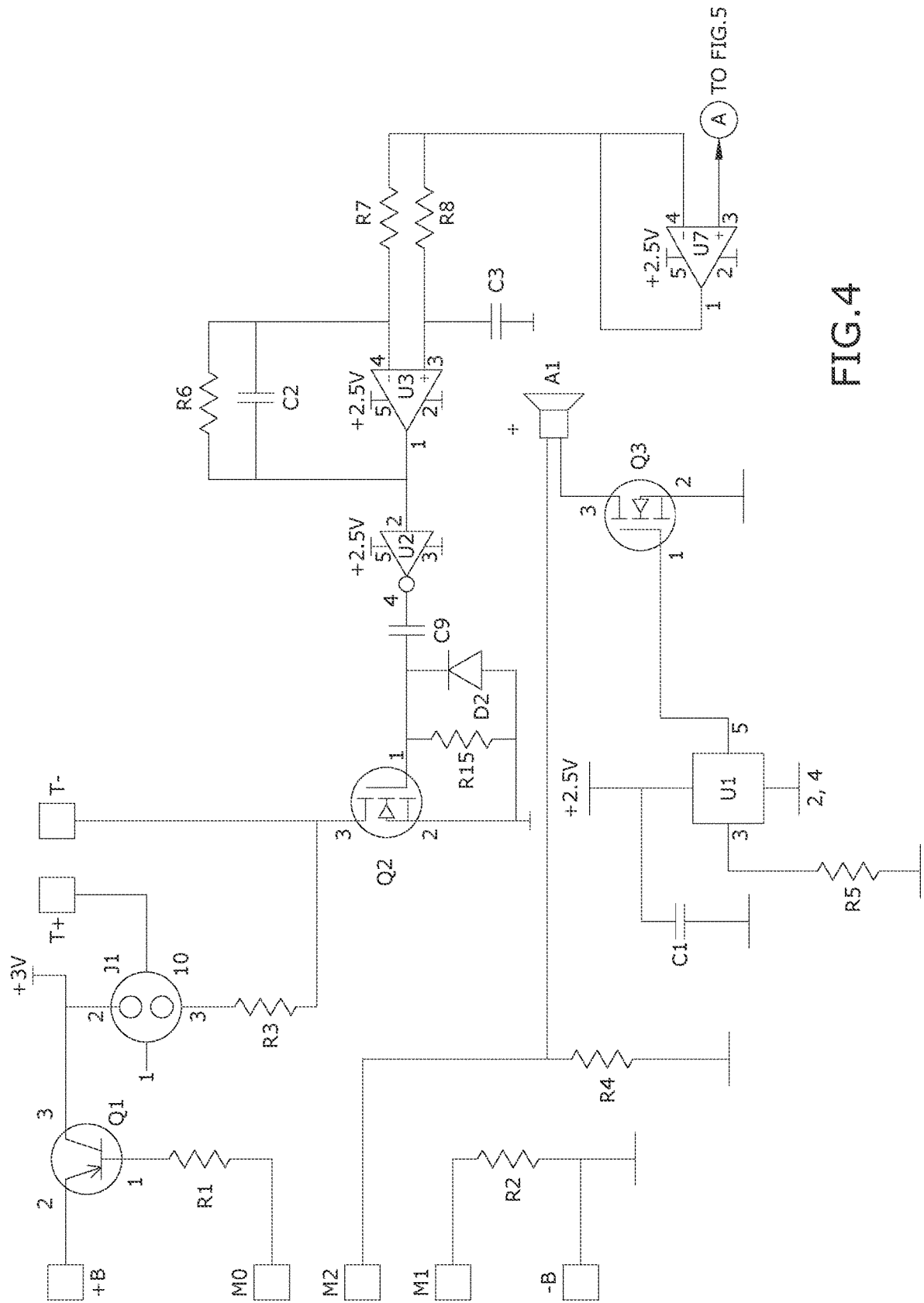
FIG. 4 is a schematic view of circuitry therefor.

Referring to FIGS. 1 through 7, FIG. 1 shows a block diagram of a system according to an embodiment of the present invention, comprising a probe, instrumentation, and an output device, such as an earphone. The probe generally has an infrared IR emitter, a sensor, and a tactile transducer, e.g., a vibration motor M, activated by the sensor when the sensor receives reflected IR light. The sensor is operative to detect a heartbeat. The instrumentation may include components to process the signal from the sensor (including converting the signal to a digital pulse), including an auto-leveling circuit, a high gain amplifier U3, and a pulse generation circuit U2, Q2. The amplifier shown in FIG. 4 is an op-amp with a gain of about 2000 V/V. Resistor R6 is 10 Mw and resistor R7 is 5 kw. The auto-leveling circuit compensates for ambient light variations surrounding the sensor and pigment variations in the metacarpal or metatarsal pads of the subject (e.g., a cat or a dog) by adjusting the direct current (DC) bias with a current regulator Q4. In other words, the auto-leveling circuit maintains a linear DC bias of the phototransistor. The high gain amplifier U3 amplifies the signal (or current) from the auto leveling circuit. The pulse generation circuit U2, Q2 drives a vibration motor or an earphone when a heartbeat is detected by the sensor, see FIG. 6. In some embodiments, the vibration motor M may be decoupled when the earphone is inserted into an earphone jack J1. As shown in FIG. 1, the instrumentation may include a switch therefor as part of the earphone jack J1, operative to switch transmission of a signal from the infrared detector between the tactile transducer and the earphone jack. The instrumentation may also include a battery detector, a power indicator, a timer, and a tone emitter (i.e., a beeper).

FIG. 2 provides an oscilloscopic display depicting a signal produced by the optical sensor juxtaposed with pulsed output delivered via either a tactile transducer, an earphone, or a combination thereof.

An illustration of the device 10 according to an embodiment of the invention is shown in FIG. 3. A probe 12 may comprise an optical sensor and a tactile transducer. The probe 12 may be connected to a housing 16 containing instrumentation, which may include a power indicator 18, e.g., a pilot lamp, an earphone jack 20, and a power switch 22, e.g., a power-on, dual mode rocker switch with a center off setting. A cable 24 may be provided to electrically link the probe to the instrumentation. For example, an about 1-meter cable may be considered suitable.

Figure 5:
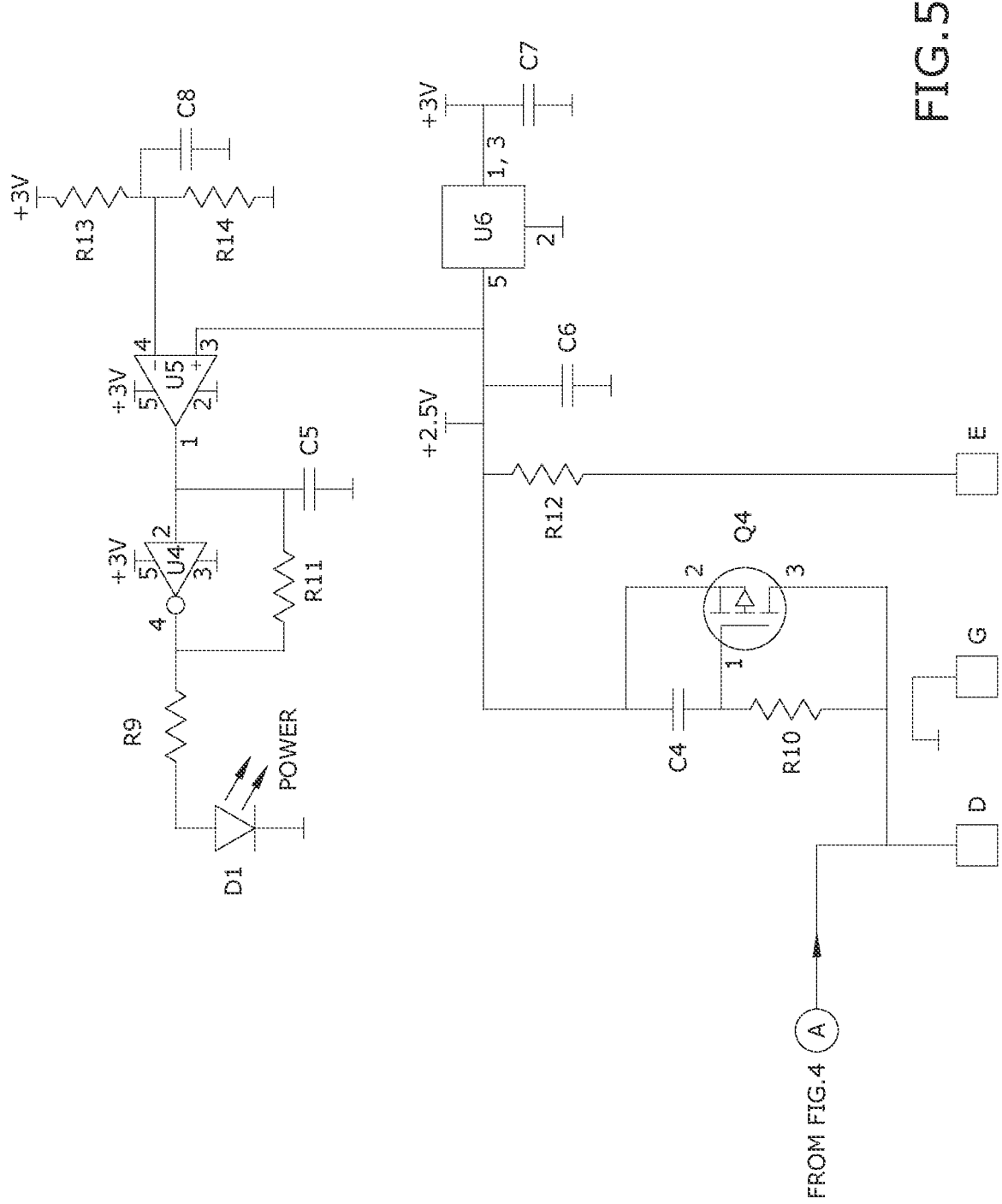
FIG. 5 is a continuation schematic of circuitry therefor.

Details of the instrumentation and probe circuits for the device of FIG. 3 are shown in FIGS. 4 and 5. The circuitry may include additional analog devices selected from, and not limited to, the group consisting of an operational amplifier (op-amp), a comparator, a voltage regulator, an LED, a phototransistor, and combinations thereof.

As shown in FIG. 4, the inventive probe may have two modes of operation, a silent mode M1 and a timer mode M2. The modes are selected by a single pole, double throw rocker switch S1 (see FIG. 7) with a center-off position. During blood pressure measurements, M1 is selected as the means to detect a pulse while maintaining a quiet environment. If only the pulse rate is needed, M2 is selected. In this mode, the timer integrated circuit U1 is enabled. U1 pulses an audio transducer A1 via circuit Q3, e.g., every 15 seconds, emitting a beep, e.g., with a duration of about 50 ms. The measurer counts the number of pulses, either tactilely or aurally, between two successive beeps, separated by 15 seconds, e.g., then multiplies the number by four, e.g., to get beats per minute. This provides a convenient way of determining the heart rate without watching a clock. Veterinarians often count pulses over a 15 second period in a clinic setting to measure the heart rate. Typically, the resting heart rate of a cat is about 120 beats per minute. In this case, about 30 pulses may be counted in 15 seconds.

Figure 6:
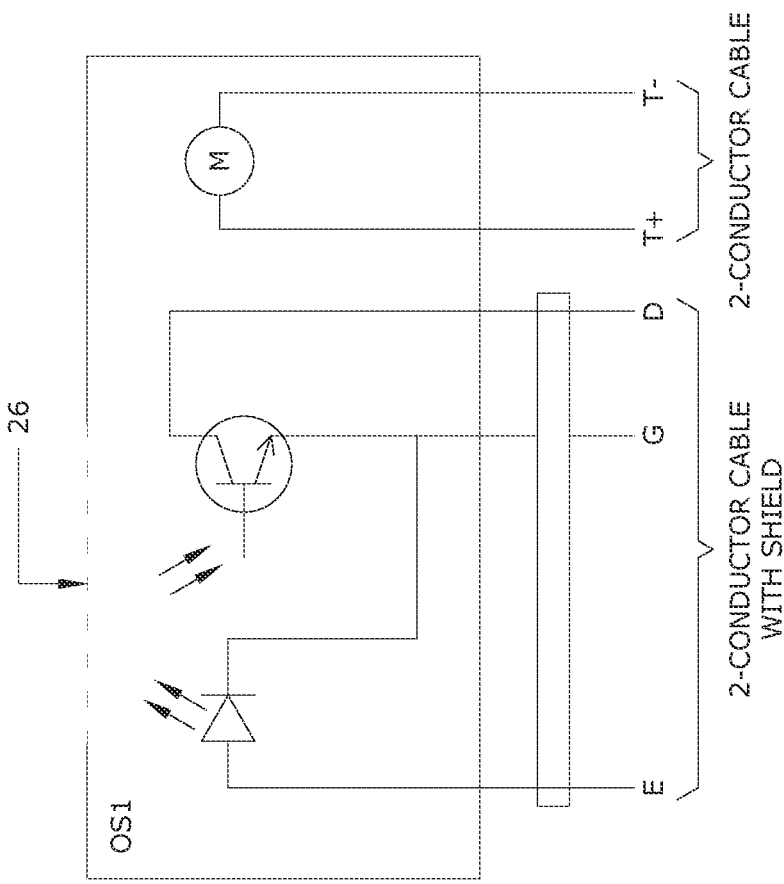
FIG. 6 is a schematic view of a probe thereof.

FIG. 6 shows a schematic view of the components of the probe 12, illustrating infrared emitted through a window 26 and reflected infrared returning through the window 26. FIG. 6 also illustrates interconnections between the probe 12 and the cable 24.

Figure 7:
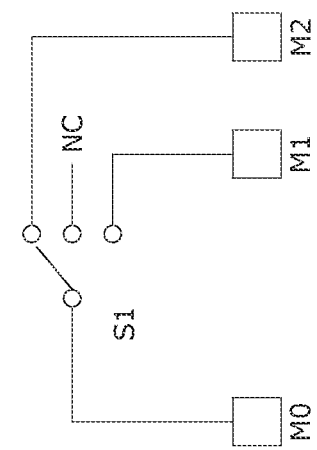
FIG. 7 is a schematic view of a power switch therefor.

FIG. 7 is a schematic view of the components of the power switch 22.

It should be understood, of course, that the foregoing relates to exemplary embodiments of the invention and that modifications may be made without departing from the spirit and scope of the invention as set forth in the following claims.

What is claimed is:

1. An arterial pulse detection system, comprising:
   a probe having a probe housing with a surface having a window formed therein, said surface being configured for placement on a paw pad, containing:
   (a) a reflective optical sensor mounted in the probe housing and aligned with the window, said reflective optical sensor comprising an infrared emitter and an infrared detector; and
   (b) a tactile transducer mounted within the probe housing adjacent to the reflective optical sensor, said tactile transducer being operative to convert a signal received from the infrared detector corresponding to an arterial pulse sensed by the reflective optical sensor to a tactile pulsed output; and
   instrumentation electrically connected to the reflective optical sensor and the tactile transducer, including an auto-leveling circuit comprising a current regulator, said auto-leveling circuit being operative to maintain a linear direct current bias from the infrared detector.

2. The arterial pulse detection system of claim 1, further comprising a counting timer operative to beep after a predetermined time.

3. The arterial pulse detection system of claim 1, further comprising a potentiometer operative to modulate a volume.

4. The arterial pulse detection system of claim 1, further comprising a high gain amplifier operative to amplify current from the infrared detector.

5. The arterial pulse detection system of claim 1, further comprising additional analog devices selected from the group consisting of an operational amplifier, a comparator, a voltage regulator, a light emitting diode, a phototransistor, and combinations thereof.

6. The arterial pulse detection system of claim 1, wherein the optical sensor and the tactile transducer are electrically connected with the instrumentation by a cable.

7. The arterial pulse detection system of claim 1, wherein the instrumentation is contained within an instrumentation housing.

8. The arterial pulse detection system of claim 7, wherein the instrumentation housing further comprises a power switch operative to activate the instrumentation.

9. The arterial pulse detection system of claim 7, wherein the instrumentation housing further comprises an earphone jack.

10. The arterial pulse detection system of claim 9, wherein the instrumentation housing further comprises a mode switch operative to switch transmission of a signal from the infrared detector between the tactile transducer and the earphone jack.

11. The arterial pulse detection system of claim 1, wherein the tactile transducer is a vibration motor.

\* \* \* \* \*